US012807549B2

(12) United States Patent
Kang et al.

(10) Patent No.: US 12,807,549 B2
(45) **Date of Patent: *Nov. 24, 2026**

(54) PROCESS FOR THE PURIFICATION OF FLUORINATED OLEFINS

(71) Applicant: Solvay SA, Brussels (BE)

(72) Inventors: Joo-Hee Kang, Lyons (FR); Christian Groeber, Bad Friedrichshall (DE); Michael Pittroff, Ahlten (DE); Denis Revelant, Genas (FR)

(73) Assignee: Solvay SA, Brussels (BE)

( * ) Notice: Subject to any disclaimer, the term of this patent is extended or adjusted under 35 U.S.C. 154(b) by 684 days.

This patent is subject to a terminal disclaimer.

(21) Appl. No.: 18/247,721

(22) PCT Filed: Sep. 28, 2021

(86) PCT No.: PCT/EP2021/076577

§ 371 (c)(1),
(2) Date: Apr. 3, 2023

(87) PCT Pub. No.: WO2022/069435

PCT Pub. Date: Apr. 7, 2022

(65) Prior Publication Data

US 2024/0025825 A1 Jan. 25, 2024

(30) Foreign Application Priority Data

Oct. 2, 2020 (EP) .................................... 20199794

(51) Int. Cl.

| | |
|---|---|
| ***C07C 17/389*** | (2006.01) |
| ***B01D 15/20*** | (2006.01) |
| ***C09K 13/00*** | (2006.01) |

(52) U.S. Cl.

CPC .......... *C07C 17/389* (2013.01); *B01D 15/203* (2013.01); *C09K 13/00* (2013.01)

(58) Field of Classification Search

CPC ....... C07C 17/389; C07C 21/10; C09K 13/00; B01D 15/203

See application file for complete search history.

(56) References Cited

U.S. PATENT DOCUMENTS

| | | | |
|---|---|---|---|
| 6,403,491 | B1 | 6/2002 | Liu et al. |
| 6,544,319 | B1 | 4/2003 | Krouse et al. |

FOREIGN PATENT DOCUMENTS

| | | | |
|---|---|---|---|
| CN | 106349008 | A | 1/2017 |
| CN | 107032949 | A | 8/2017 |
| CN | 111285753 | A | 6/2020 |
| EP | 1329442 | A1 | 7/2003 |
| EP | 3632883 | A1 | 4/2020 |
| WO | 2020137845 | A1 | 7/2020 |
| WO | 2020164912 | A1 | 8/2020 |

OTHER PUBLICATIONS

Office Action issued in Taiwanese Application No. 110136255, mailed on Jan. 10, 2025 (15 pages).

Office Action issued in Chinese Application No. 2021800716467, mailed on May 19, 2025 (8 pages).

*Primary Examiner* — Jafar F Parsa

(74) *Attorney, Agent, or Firm* — Osha Bergman Watanabe & Burton LLP

(57) ABSTRACT

The present invention relates to a process for the purification of fluorinated olefins, in particular hexafluoro-1,3-butadiene, comprising a step wherein a liquid mixture comprising hexafluoro-1,3-butadiene in liquid phase is contacted with at least one adsorbent having an average pore size of less than 10 Å.

11 Claims, 1 Drawing Sheet

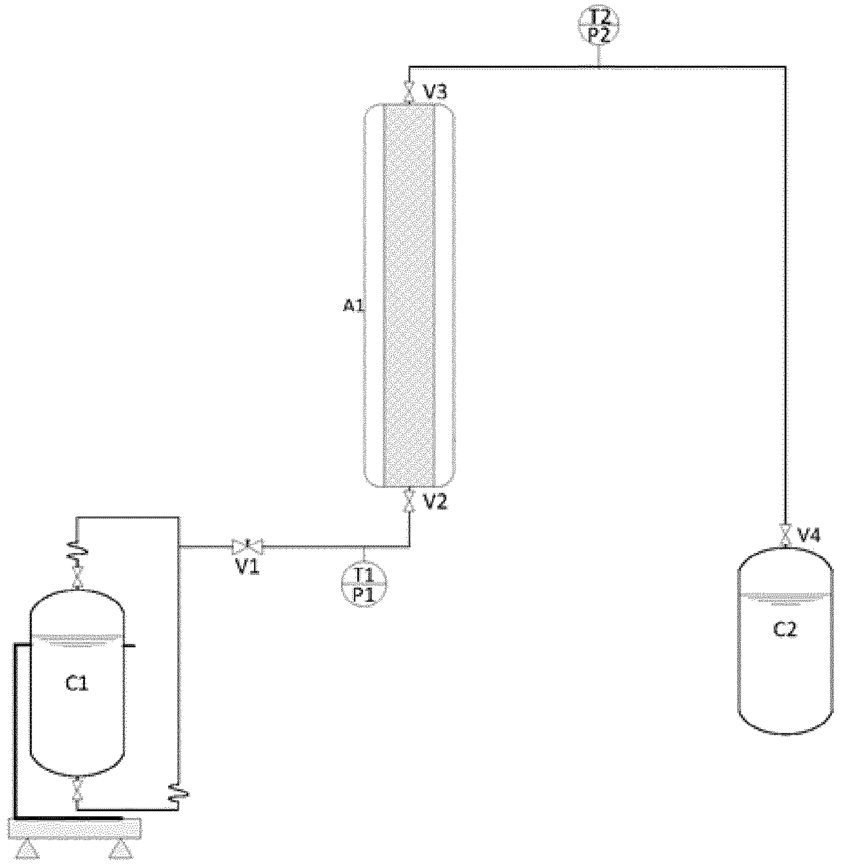
T2
P2
V3
A1
V2
V1
T1
P1
C1
V4
C2

PROCESS FOR THE PURIFICATION OF FLUORINATED OLEFINS

The present invention relates to a process for the purification of fluorinated olefins, such as, especially, hexafluoro-1,3-butadiene.

Hexafluoro-1,3-butadiene is a colorless, gaseous unsaturated fluorocarbon with an alternating double bond. It is an etchant showing very high performance for plasma, ion beam, or sputter etching in semiconductor devices manufacturing. Due to its short atmospheric lifetime (<1 day), its negligible global warming potential, and its inertness to the stratospheric ozone layer, hexafluoro-1,3-butadiene is an environmentally compatible gas. Hexafluoro-1,3-butadiene is marketed by Solvay under the brand name Sifren® 46.

Hexafluoro-1,3-butadiene employed in the semiconductor industry must be of extremely high purity. To this end, EP1329442A1 describes a process for the purification of hexafluoro-1,3-butadiene in gas phase, using certain adsorbents with low average pore diameter, particularly molecular sieve 5 Å, since the hexafluoro-1,3-butadiene is apparently excluded from the adsorbent while the impurities are adsorbed and thus, avoiding deleterious decomposition reactions from occurring.

WO2020/164912A1 describes a process for the purification of fluorinated olefins, such as, especially, hexafluoro-1,3-butadiene, using at least two adsorbents having an average pore size of above 6 Å, especially a combination of silica gel and molecular sieve 13X. The process is carried out on hexafluor-1,3-butadiene in gas phase as well.

Hexafluoro-1,3-butadiene is an extremely flammable gas: it is classified in category 1 based on the GHS criteria. It has a lower explosion limit in mixture with air between 5 and 6 mol %. As a consequence, the running of the known purification processes of hexafluoro-1,3-butadiene may be quite challenging from a safety viewpoint. It may be hard especially to detect a possible leakage of hexafluoro-1,3-butadiene in gaseous form in the purification line. If such a leakage happened in a place not ventilated enough, it could cause a fire or an explosion. The purification units working with hexafluoro-1,3-butadiene in gas phase therefore require to put in place important safety measures and features. This represents heavy costs in terms of maintenance and facilities investments.

Additionally, the existing purification processes based on the use of adsorbents require a step of activation thereof prior to the purification step, mainly for removing residual moisture. The activation treatment usually consists in a heat treatment at high temperature, typically ranging from 250° C. to 400° C., under a dry inert atmosphere. This step constitutes a supplementary production cost as it wastes energy, time and it requires managing effluents.

Thus, there is still a need for an improved process for the purification of hexafluoro-1,3-butadiene. Consequently, one objective of the present application is to propose an improved process for the purification of hexafluoro-1,3-butadiene, suitable to solve at least one and preferably several of the above mentioned problems. Among others objectives, the present invention aims at providing a safe, fast, simple, economical and/or environment-friendly purification process, which can be run efficiently at industrial scale, in compact facilities, as well as providing an hexafluoro-1,3-butadiene having an improved purity, at the very least a purity suitable with electronics applications.

These and other objectives are achieved by the process according to the present invention.

Accordingly, a first aspect of the present invention concerns a process for the purification of hexafluoro-1,3-butadiene comprising a step wherein a liquid mixture comprising hexafluoro-1,3-butadiene in liquid phase is contacted with at least one adsorbent having an average pore size of less than 10 Å. The average pore size may be measured by conventional methods known by a skilled person, in particular by nitrogen adsorption porosimetry.

The process of the invention has various advantages. Among others, it can be implemented in a simple, economical and very compact facility, which reduces the construction cost. A potential leakage of hexafluoro-1,3-butadiene can be easily detected as it is in the form of a liquid. Energy saving can be made, as the evaporation of the crude hexafluoro-1,3-butadiene and the condensation of the purified hexafluoro-1,3-butadiene required when working in gas phase are avoided. The purification process of hexafluoro-1,3-butadiene in liquid phase is more effective than in gas phase, as the impurities have a higher concentration due to the higher density of the liquid compared to the gas phase. This improves adsorption by increasing the driving forces to pass from the liquid to the solid.

FIG. 1 shows a flow diagram of an apparatus suitable for performing the process according to the present invention.

The liquid mixture to be purified may contain various impurities in liquid phase in admixture with the hexafluoro-1,3-butadiene, such as hydrohalogenocarbons, especially hydrofluorocarbons and/or hydrochlorofluorocarbons, more particularly hydrohalogenoolefins, especially hydrofluoroolefins such as 1,1,3,4,4-pentafluoro-1,3-butadiene and/or isomers thereof (commonly referred to as C4HF5 thereafter), 1,1,4,4-tetrafluoro-1,3-butadiene and/or isomers thereof (commonly referred to as C4H2F4 thereafter). The liquid mixture, in the framework of this invention, may be composed of hexafluoro-1,3-butadiene in liquid phase as major component and of the various possible impurities contained therein, equally in liquid phase. Said impurities may come from the formation of byproducts, from residual solvents, unreacted starting materials and/or partially unreacted starting materials.

Without being particularly limited, the initial purity of the raw hexafluoro-1,3-butadiene to be purified by the process according to the invention may be equal to or greater than 90% by volume, in particular equal to or greater than 95% by volume, more particularly equal to or greater than 98% by volume, even more particularly equal to or greater than 99% by volume, relatively to the total volume of raw hexafluoro-1,3-butadiene. Especially, the raw hexafluoro-1,3-butadiene may comprise from 0 ppmv to 1500 ppmv, in particular from 5 ppmv to 1000 ppmv of C4H2F4. The raw hexafluoro-1,3-butadiene may comprise from 0 ppmv to 1000 ppmv, in particular from 5 to 500 ppmv of C4HF5.

Said at least one adsorbent is selected from adsorbents having an average pore size of less than 10 Å. It is believed that such an adsorbent is effective to trap most of all the possible impurities likely to be present in the raw hexafluoro-1,3-butadiene. Above 10 Å, the hexafluoro-1,3-butadiene itself could be at least partially adsorbed: it could decompose and generate thereby further impurities.

According to one sub-embodiment, said at least one adsorbent may be selected from adsorbents having an average pore size of more than 2 Å and less than 8 Å, in particular of more than 3 Å and less than 6 Å and more particularly of more than 3 Å and less than 5,5 Å. It is believed that adsorbents having such an average pore size are very suitable to trap the main impurities potentially present in the raw hexafluoro-1,3-butadiene, such as C4H2F4 and/or C4HF5.

Suitable adsorbents that can be used in the framework of the invention include zeolites having a pore size of less than 10 Å, especially the ones having eight-membered-ring pores such as Zeolite P, Gmelinite, synthetic Chabazite, in particular SSZ-13 or SSZ-62; zeolite 5A; zeolite MFI. Zeolite type adsorbents having eight-membered-ring pores are preferred and among them, synthetic Chabazite is particularly advantageous, especially regarding its selectivity towards C4H2F4 and/or C4HF5, which are the main impurities likely to be present in the hexafluoro-1,3-butadiene to be purified. A very suitable synthetic Chabazite includes the HCZC S (H-form) from CLARIANT.

The hexafluoro-1,3-butadiene is in liquid phase when contacted with said at least one adsorbent. Accordingly, the contacting step is preferably performed in suitable conditions of pressure, temperature and/or flow rate to maintain the hexafluoro-1,3-butadiene and the possible impurities contained therein in the liquid state.

Preferably, the process is conducted at an initial pressure of equal to or above 0.1 bar (abs.) and equal to or below 10 bar (abs.), in particular from 0.1 bar (abs.) to 5 bar (abs.).

Also preferably, the process is conducted at an initial temperature of equal to or above 5° C. and equal to or below 40° C., in particular from 5° C. to 30° C.

Also preferably, the process is conducted at an initial flow rate ranging from 2 g/min to 200 g/min, in particular from 2 to 150 g/min, more particularly from 2 to 100 g/min, even more particularly from 2 to 50 g/min.

The contacting step may in particular be operated at an initial pressure of equal to or above 0.1 bar (abs.) and equal to or below 10 bar (abs.), at an initial temperature of equal to or above 5° C. and equal to or below 40° C. and at an initial flow rate ranging from 2 g/min to 200 g/min. The contacting step may more particularly be operated at an initial pressure of equal to or above 0.1 bar (abs.) and equal to or below 5 bar (abs.), at an initial temperature of equal to or above 5° C. and equal to or below 30° C. and at an initial flow rate ranging from 2 g/min to 50 g/min.

The term "initial" as used herein is intended to denote respectively the temperature, pressure and flow rate of the liquid mixture before coming into contact with said at least one adsorbent having an average pore size of less than 10 Å.

According to one embodiment, said at least one adsorbent used within the purification process of the invention is not pre-treated, in particular by any heat treatment, before being contacted with the liquid mixture. Contrary to the purification processes of the state of the art, wherein a pre-treatment often called "activation" which consists in keeping the adsorbent at an elevated temperature, typically between 150 and 400° C., under inert atmosphere to remove moisture from the adsorbent before its first use, the purification process of the invention does not require such a step. It advantageously enables production savings, as it avoids a waste of time, of energy and the management of effluents (mainly water, carbon dioxide and the inert gas used).

The process of the invention can comprise one or more additional purification steps, before or after the contacting step with said at least one adsorbent, using other types of adsorbents than the ones described above or even different purification means. Among the possible means which could be used and without being specifically limited to these means, mention can be made of other adsorbents like silica gel, zeolite 3A, zeolite 5A, zeolite 13X, zeolite MFI, zeolite P, gmelinite, activated alumina, activated carbon and the like.

According to one specific embodiment, the process of the invention does not comprise any other purification step than the contacting step with said at least one adsorbent having an average pore size of less than 10 Å. It is nevertheless possible to use more than one adsorbent having an average pore size of less than 10 Å, which can be the same or different from each other. The further adsorbent(s) used can be advantageously selected among the list of suitable adsorbents having an average pore size of less than 10 Å listed above. Other less preferred adsorbents can be used alternatively.

If more than one adsorbent is used in the purification process of the invention, the adsorbents can be present in different zones in the same adsorber cartridge. Thus, only one adsorber cartridge may be used in the purification process and the adsorbents may be located within the one cartridge in different zones, preferably in subsequent zones allowing the liquid mixture to be in contact with one adsorbent after the other. Alternatively, the adsorbents may be present in different adsorber cartridges, so that the liquid mixture can be brought into contact with the adsorbents one after the other and the adsorbents can be regenerated individually.

The final purity of the hexafluoro-1,3-butadiene achieved by the process according to the invention may be equal to or greater than 99.9% by volume, preferably equal to or greater than 99.95% by volume, more preferably equal to or greater than 99.98% by volume, and most preferably equal to or greater than 99.99% by volume, relatively to the total volume of the hexafluoro-1,3-butadiene.

The total amount of hydrofluorocarbons potentially remaining in the purified hexafluoro-1,3-butadiene may be lower or equal to 1400 ppmv, in particular lower or equal to 1000 ppmv, in particular lower or equal to 600 ppmv, in particular lower or equal to 500 ppmv, in particular lower or equal to 300 ppmv, in particular lower or equal to 150 ppmv. The total amount of hydrofluorocarbons potentially remaining in the purified hexafluoro-1,3-butadiene may be equal to or greater than 0 ppmv, equal to or greater than 1 ppmv, in particular equal to or greater than 10 ppmv, in particular equal to or greater than 30 ppmv. It may be measured by conventional methods, such as gas chromatography or mass spectroscopy.

The total amount of C4H2F4 potentially remaining in the purified hexafluoro-1,3-butadiene may be lower or equal to 400 ppmv, in particular lower or equal to 200 ppmv, in particular lower or equal to 100 ppmv, in particular lower or equal to 50 ppmv, in particular lower or equal to 10 ppmv, in particular lower or equal to 6 ppmv. The total amount of C4H2F4 potentially remaining in the purified hexafluoro-1,3-butadiene may be equal to or greater than 0 ppmv. It may be in the limit of detection of the apparatus used to quantify this impurity. It may for instance be equal to or greater than 0.001 ppmv, in particular equal to or greater than 0.1 ppmv, in particular equal to or greater than 1 ppmv. It may be measured by any known method such as gas chromatography or mass spectroscopy.

The total amount of C4HF5 potentially remaining in the purified hexafluoro-1,3-butadiene may be lower or equal to 80 ppmv, in particular lower or equal to 70 ppmv, in particular lower or equal to 60 ppmv, in particular lower or equal to 55 ppmv, in particular lower or equal to 50 ppmv, The total amount of C4HF5 potentially remaining in the purified hexafluoro-1,3-butadiene may be equal to or greater than 0 ppmv, equal to or greater than 1 ppmv, in particular equal to or greater than 10 ppmv. It may be measured by any known method such as gas chromatography or mass spectroscopy.

The purification process can be repeated as many times as necessary to achieve the desired purity for the final hexafluoro-1,3-butadiene. In the purification unit designed for implementing the process of the invention, a recycling loop can therefore be settled to recover the purified hexafluoro-1,3-butadiene downstream of the purification unit and send it back upstream of the purification unit. According to one embodiment, the purification process of the invention, which may consist in the contacting step with said at least one adsorbent, is run only one time. It is believed that the process of the invention is suited to achieve a very good purity in a single passage of the liquid mixture comprising hexafluoro-1,3-butadiene.

The purification process according to the invention may comprise a regeneration step of said at least one adsorbent. The regeneration step may comprise or consist in a heat treatment thereof, preferably at a temperature ranging from 200 to 400° C., more preferably from 250 to 350° C., even more preferably from 280 to 300° C. The pressure conditions are not particularly limited: the regeneration step may be advantageously performed at atmospheric pressure.

The hexafluoro-1,3-butadiene purified according to the present invention can be used neat. However, it is often desired to use the hexafluoro-1,3-butadiene of the present invention as an admixture with other fluorinated etching gases to control the carbon/fluoro ratio of the gas mixture. Additionally, mixtures with suitable inert gases like nitrogen, argon or xenon or with oxygen might be desired.

Accordingly, a further aspect of the present invention is a process for the production of a gas mixture according to the present invention, comprising the process for the purification of hexafluoro-1,3-butadiene described above and subsequently, mixing the purified hexafluoro-1,3-butadiene with a further gas selected from the group consisting of an inert gas, oxygen and another fluorinated etching gas as well as the gas mixture formed in such a process.

In particular, one object of the invention is a gas mixture comprising hexafluoro-1,3-butadiene and at least one further gas selected from the group consisting of an inert gas, oxygen and another fluorinated etching gas, wherein the volume ratio of hydrofluorocarbons is lower or equal to 500 ppmv, in particular lower or equal to 300 ppmv, in particular lower or equal to 150 ppmv, relatively to the total volume of the gas mixture.

Preferably, the volume ratio of $C4H2F4$ possibly present in said gas mixture is lower or equal to 50 ppmv, in particular lower or equal to 10 ppmv, in particular lower or equal to 5 ppmv, relatively to the total volume of the gas mixture.

Preferably, the volume ratio of $C4HF5$ possibly present in said gas mixture is lower or equal to 70 ppmv, in particular lower or equal to 60 ppmv, in particular lower or equal to 55 ppmv, in particular lower or equal to 50 ppmv, relatively to the total volume of the gas mixture.

The lower limits of some impurities may be in the limit of quantification of the measurement tool. For hydrofluorocarbons in general, including the two specific ones mentioned above, the limit of quantification shall appear under 4 ppmv, as measured by GC.

The inventive gas mixtures can easily be prepared by condensing or pressing the desired amounts of hexafluoro-1,3-butadiene and any other desired gas into a pressure tank.

Furthermore, the invention concerns a process for the production of a semiconductor material, a solar panel, a flat panel or a microelectromechanical system, or a process for cleaning the chamber of an apparatus used for semiconductor manufacturing using the hexafluoro-1,3-butadiene purified according to this invention or the gas mixture according to this invention. The preferred use is in the production of a microelectromechanical system.

Should the disclosure of any patents, patent applications, and publications which are incorporated herein by reference conflict with the description of the present application to the extent that it may render a term unclear, the present description shall take precedence.

The invention will be illustrated in more detail with reference to FIG. 1 and the following Example, but it should be understood that the present invention is not deemed to be limited thereto.

Crude hexafluoro-1,3-butadiene was provided by Solvay under the brand name Sifren® 46. It was analyzed by gas chromatography and mass spectroscopy to quantify the main organic impurities contained therein. The results are indicated in Table 1. The adsorbent used was Chabazite HCZC S (H-form) supplied by CLARIANT, having an average pore size of 3.8 Å. It was not thermally pre-treated before usage and used as it was.

FIG. 1 shows a suitable apparatus which was used to run the process according to the present invention. A source tank C1, having a 1 L capacity, intended to be loaded with the crude hexafluoro-1,3-butadiene, was connected to a stainless steel column A1 containing the adsorbent bed, charged with 82.07 g of Chabazite. The column had an internal diameter of 18 mm and a length of 406 mm. It was double jacketed and connected to a cooling bath for being able to cool down the bed in case of an exothermic reaction inside. The column A1 was connected to a receiver tank C2 for collecting the purified hexafluoro-1,3-butadiene, submersed in a cooling bath at 5° C. (mix of dry ice and acetone). Pressure gauges P1, P2 and thermocouples T1, T2 were set before and after column A1 as shown on FIG. 1. All piping was made of stainless steel. Before flowing the hexafluoro-1,3-butadiene into the apparatus, the tightness thereof was checked under vacuum. Afterwards, the source tank C1 was loaded with 500 g of crude hexafluoro-1,3-butadiene (as measured with a balance). The pressure inside the source tank was set at 2.8 bar abs and the temperature within the source tank was set at room temperature (about 22° C.) so as to keep the hexafluoro-1,3-butadiene in liquid phase. The crude hexafluoro-1,3-butadiene in liquid state was then allowed to flow through column A1 and the purified hexafluoro-1,3-butadiene in liquid state was collected in receiver tank C2. The flow rate was manually set at about 5 g/min by adjusting needle valves V1, V2 and V3 accordingly. During the run, a pressure of 2.8 bar (abs.) was measured at pressure gauge P1 and a temperature of 22° C. was measured at thermocouple T1. A pressure of 1.15 bar (abs.) was measured at pressure gauge P2 and a temperature of 26° C. was measured at thermocouple T2. After all the crude hexafluoro-1,3-butadiene was passed through column A1, receiver tank 2 was isolated by closing valve V4 and then allowed to warm to room temperature.

A sample of the purified hexafluoro-1,3-butadiene in receiver tank 2 was analyzed by gas chromatography and mass spectroscopy to quantify the main organic impurities remaining therein. The results are indicated in Table 1.

TABLE 1

| Analysis results | | |
|---|---|---|
| impurites (ppmv) relative to the total volume of hexafluoro-1,3-butadiene | Source tank C1 | Receiver tank C2 |
| $C_4H_2F_4$ | 505 | <5 |
| $C_4HF_5$ | 91 | 43 |
| Total hydrofluorocarbons | <1500 | <120 |

The invention claimed is:

1. A process for the purification of hexafluoro-1,3-butadiene comprising a step wherein a liquid mixture comprising hexafluoro-1,3-butadiene in liquid phase is contacted with at least one adsorbent having an average pore size of less than 10 Å.

2. The process according to claim 1, wherein said at least one adsorbent has an average pore size of more than 2 Å and less than 8 Å.

3. The process according to claim 1, wherein said at least one adsorbent is a zeolite.

4. The process according to claim 3, wherein the zeolite has eight-membered-ring pores.

5. The process according to claim 4, wherein the zeolite is synthetic Chabazite.

6. The process according to claim 1, wherein the liquid mixture is contacted with said at least one adsorbent at an initial pressure of equal to or above 0.1 bar (abs) and equal to or below 10 bar (abs).

7. The process according to claim 1, wherein the liquid mixture is contacted with said at least one adsorbent at an initial temperature of equal to or above 5° C. and equal to or below 40° C.

8. The process according to claim 1, wherein the liquid mixture is contacted with said at least one adsorbent at a flow rate of equal to or above 2 g/min and equal to or below 200 g/min.

9. The process according to claim 1, wherein said at least one adsorbent is not thermally treated before being contacted with the liquid mixture.

10. The process according to claim 1, comprising a regeneration step of said at least one adsorbent, the regeneration step comprising a heat treatment of said at least one adsorbent at a temperature ranging from 200 to 400° C.

11. A process for the production of a gas mixture comprising the process according to claim 1 and subsequently, mixing the purified hexafluoro-1,3-butadiene with a further gas selected from the group consisting of an inert gas, oxygen and another fluorinated etching gas.

* * * * *